United States Patent
Liang et al.

(10) Patent No.: US 9,468,638 B2
(45) Date of Patent: Oct. 18, 2016

(54) ITRACONAZOLE FORMULATIONS

(75) Inventors: Dong Liang, Pearland, TX (US); Lei Wu, Houston, TX (US); Mathew Kizhakkekara Joseph, Houston, TX (US); Jyothy Anie John, Houston, TX (US)

(73) Assignee: Texas Southern University, Houston, TX (US)

( * ) Notice: Subject to any disclaimer, the term of this patent is extended or adjusted under 35 U.S.C. 154(b) by 634 days.

(21) Appl. No.: 13/200,285

(22) Filed: Sep. 22, 2011

(65) Prior Publication Data

US 2012/0077824 A1   Mar. 29, 2012

Related U.S. Application Data

(60) Provisional application No. 61/403,981, filed on Sep. 24, 2010.

(51) Int. Cl.
*A61K 31/496* (2006.01)
*A61K 9/00* (2006.01)
*A61K 47/10* (2006.01)
*A61K 47/26* (2006.01)
*A61K 47/44* (2006.01)

(52) U.S. Cl.
CPC .......... *A61K 31/496* (2013.01); *A61K 9/0019* (2013.01); *A61K 47/10* (2013.01); *A61K 47/26* (2013.01); *A61K 47/44* (2013.01)

(58) Field of Classification Search
CPC .... A01N 43/26; A01N 43/60; A01N 43/653; A61K 31/357; A61K 31/4196; A61K 31/496; A61K 47/10; A61K 47/26; A61K 47/44; A61K 9/0019; C07D 241/04; C07D 249/08; C07D 317/04

USPC .......... 514/254.05, 384, 467; 544/366; 548/263.2; 549/448

See application file for complete search history.

(56) References Cited

U.S. PATENT DOCUMENTS

| | | | |
|---|---|---|---|
| 6,531,139 B1 | 3/2003 | Gao et al. | |
| 2002/0119198 A1 | 8/2002 | Gao et al. | |
| 2005/0112188 A1 * | 5/2005 | Eliaz et al. | 424/450 |
| 2006/0210622 A1 | 9/2006 | Pace et al. | |
| 2007/0249520 A1 * | 10/2007 | Gore | A61K 9/0019 424/400 |

FOREIGN PATENT DOCUMENTS

CA   WO 2009095485 A1 *   8/2009   ........... A61K 9/0024

OTHER PUBLICATIONS

Yun-Seok Rhee et al., Formulation of Parenteral Microemulsion Containing Itraconazole, Arch Pharm Res, vol. 30, No. 1, p. 114-123, 2007.

* cited by examiner

*Primary Examiner* — Sarah Pihonak
(74) *Attorney, Agent, or Firm* — Benjamin Aaron Adler

(57) ABSTRACT

Provided herein is a pharmaceutical injectable formulation of itraconazole (10 mg/g) where the formulation comprises a solubilizer, a nonionic surfactant/emulsifier, a co-surfactant and a stabilizer. Further provided is a pharmaceutical formulation of itraconazole, said formulation comprising a solubilizer in a concentration of from about 20% to about 75%, a nonionic surfactant/emulsifier in a concentration of from about 20% to about 50%, a co-surfactant in a concentration from about 10% to about 45% and a stabilizer in a concentration of from about 1% to about 15%.

30 Claims, 2 Drawing Sheets

ITRACONAZOLE FORMULATIONS

CROSS-REFERENCE TO RELATED APPLICATIONS

This non-provisional application claims benefit of priority under 35 U.S.C. §119(e) of provisional application U.S. Ser. No. 61/403,981, filed Sep. 24, 2010, the entirety of which is hereby incorporated by reference.

BACKGROUND OF THE INVENTION

1. Field of the Invention

The present invention relates to the field of pharmaceutical formulations of anti-fungal drugs. More specifically, the present invention relates to novel formulations of itraconazole.

2. Description of the Related Art

Itraconazole ($C_{35}H_{38}Cl_{28}O_4$) marketed as Sporanox®, a registered trademark of Janssen Pharmaceuticals, an itraconazole formulation comprising hydroxylpropyl-b-cyclodextrin, is a triazole antifugal agent effective against three main groups of fungi: histoplasmosis, aspergillosis, and blastomycosis (1-2). All three types of fungi can cause serious damage to the lungs, heart, and other major organs if not treated or treated unsuccessfully.

The goal of antifungal therapy is to stop the spread of pathogens while they are still isolated to a single organ. When itraconazole is injected, the standard initial dose is 200 milligrams infused over the course of an hour. Another dose on the first day and single doses on each of the next five to ten days is usually sufficient to cure an infection.

Itraconazole has been used for the treatment of both systemic fungal infection and superficial mycoses (3-4), and also been successfully used in the treatment of severe necrotizing pneumonias, invasive pulmonary aspergillosis (5-6).

Itraconazole is a weakly basic compound (pKa=3.7) of high lipophilicity with a n-octanol/water partition coefficient of log $P_{o/w}$=5.66 at pH=8.1 (7-8). The drug has very poor water solubility of about 1 ng/mL at neutral pH and approximately 4 mcg/mL at pH=1 (9). Sporanox® I.V. was the only commercially available intravenous formulation of itraconazole to achieve practically applicable solubilization of the drug by hydroxylpropyl-β-cyclodextrin (HP-β-CD) complexation (Janssen Pharmaceuticals). However, sales and distribution of Sporanox® I.V. Injection in the United States was discontinued because of renal toxicity caused by its excipient, hydroxylpropyl-β-cyclodextrin. According to the package insert, each milliliter of Sporanox® I.V. contains 10 mg of itraconazole solubilzed by 400 mg of hydroxylpropyl-β-cyclodextrin as a solubilizing complex. Following intravenous administration, there was reportedly a 6-fold reduced clearance of hydroxylpropyl-β-cyclodextrin in renal impaired patients. Studies also have shown that hydroxylpropyl-β-cyclodextrin produced pancreatic adenocarcinomas in a rat carcinogenicity study.

The development of alternate clinically applicable intravenous formulations of itraconazole is difficult mainly due to its poor water solubility. Various pharmaceutically acceptable solvents have been tested for potential parenteral formulations of itraconazole (10). However, when these formulations were diluted with water, itraconazole precipitated in aqueous solution over the course of time. Thus, these formulations are not suitable for use as injections.

Several other approaches have been used in the prior art to overcome the non-solubilizing problems in an effort to find a way of delivering itraconazole intravenously. Rhee et al (11) reported an o/w microemulsion formulation of itraconazole containing benzyl alcohol and medium chain triglyceride as the oil phase. A self-emulsifying formulation of itraconazole for improved oral bioavailability has been reported (12). But microemulsions have limited water capacity and often have potential of drug precipitation at high aqueous content. A binary lipid nanoparticle formulation of itraconazole was recently developed (13) for parenteral administration of itraconazole. The nanoparticle has mean particle sizes of 190-240 nm containing triolein as the lipid core and tristearin as the solid core, alone with PEGylated phospholipid as stabilizer. Nanoparticle is a promising dosage formulation (14), but there were many practical problems to be addressed such as dosage form uniformity, macrophage endocytosis, etc. before clinical application becomes reality. Finally, a mixed polymer micellar formulation (15) was introduced using a mixed polymers including mPEG-PLA, PLA-COOH and PLA-COONa. However, actual applicability of such formulation needs further investigation.

There is, therefore, a need for improved itraconazole parenteral formulations in solvent systems that are capable of solubilizing itraconazole when diluted in an aqueous medium for intravenous administration. The present invention fulfils this longstanding need in the art.

SUMMARY OF THE INVENTION

The present invention describes the development of clinically applicable intravenous dosage formulations of itraconazole. The injectable formulation contains itraconazole with a superior anti-fungi effect, solubilizers such as polyoxyl 35 castor oil (Cremophor EL), polyoxyethylene sorbitan monooleate (Tween 80), a co-surfactant such as polyethylene glycol 400 (PEG 400), and stabilizers such as benzyl alcohol and N,N-dimethylacetamide (DMA). Pharmacokinetics of the formulation was compared with Sporanox® I.V. using rat as an animal model.

Thus, in one embodiment, the present invention provides a pharmaceutical formulation of itraconazole, wherein the formulation comprises itraconazole, a solubilizer, a nonionic surfactant/emulsifier, a co-surfactant and a stabilizer.

In another embodiment, the present invention provides a pharmaceutical formulation of itraconazole, wherein the formulation comprises itraconazole, a solubilizer in a concentration of from about 20% to about 75%, a nonionic surfactant/emulsifier in a concentration of from about 20% to about 50%, a co-surfactant in a concentration of from about 10% to about 45% and a stabilizer in a concentration of from about 1% to about 15%.

In yet another embodiment, the present invention provides a pharmaceutical formulation of itraconazole, wherein the formulation comprises itraconazole, polyoxyl hydrogenated castor oil in a concentration of from about 20% to about 75%, polyoxyethylene sorbitan monooleate in a concentration of from about 20% to about 50%, polyethylene glycol 400 in a concentration of from about 10% to about 45% and benzyl alcohol in a concentration of from about 1% to about 15%.

Other and further aspects, features, benefits, and advantages of the present invention will be apparent from the following description of the presently preferred embodiments of the invention given for the purpose of disclosure.

DETAILED DESCRIPTION OF THE INVENTION

Figure 1:
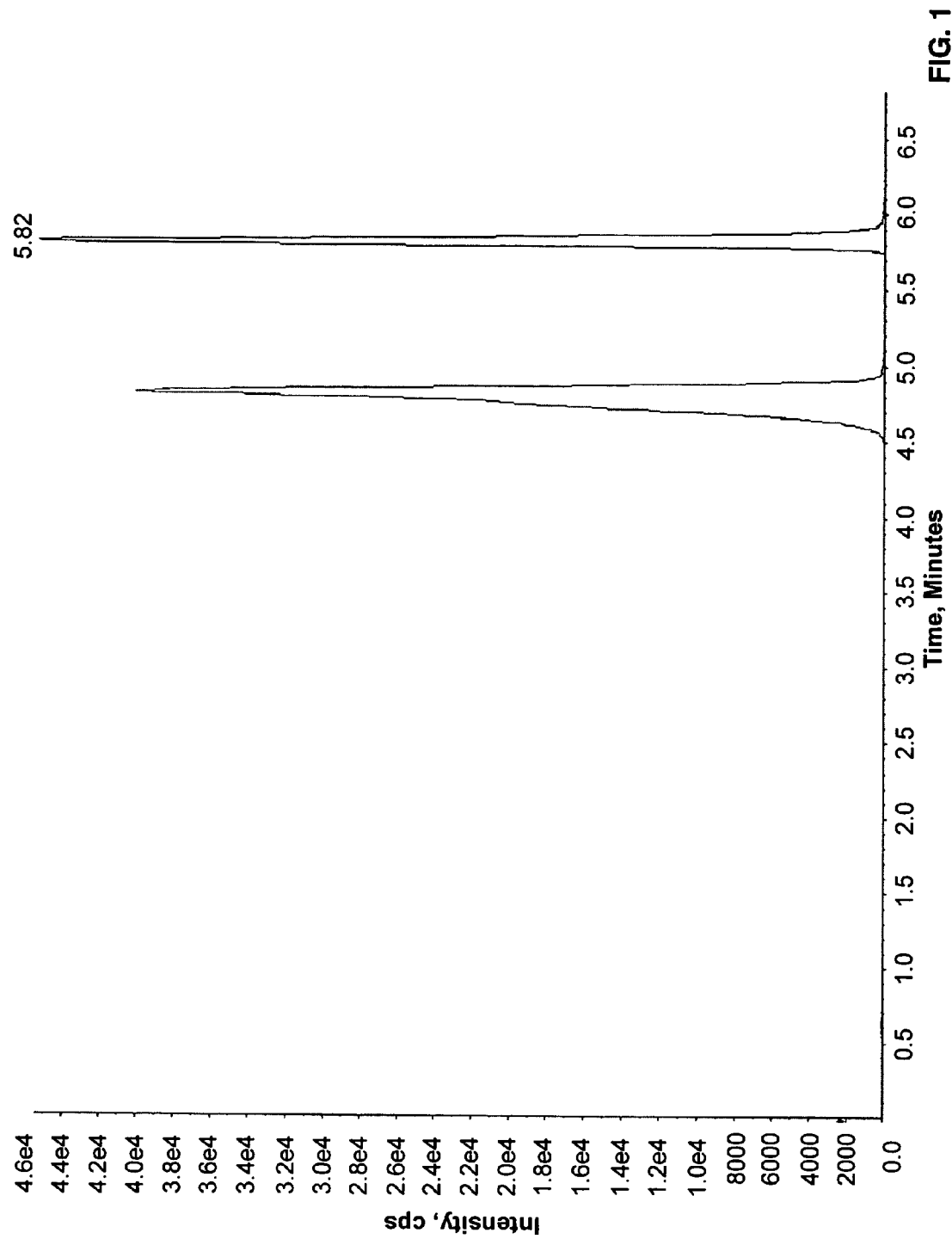
FIG. 1 shows a chromatogram of itraconazole (retention time=5.82 min) and the internal standard (retention time=4.80 min) from a rat plasma sample at 5 hours after intravenous 10 mg/kg administration of the itraconazole formulation. XIC of +MRM (2 pairs): 707.3/392.4 Da from sample 8 (itraconazole ST in RP 500 ng/ml) of itraconazole.

The present invention is directed to a pharmaceutical formulation of itraconazole, said formulation comprising itraconazole, a solubilizer, a nonionic surfactant/emulsifier, a co-surfactant and a stabilizer. Representative examples of useful solubilizers include polyethoxylated castor oil such as polyoxyl 40 hydrogenated castor oil (Cremophor RH 40), polyoxyl 60 hydrogenated castor oil (Cremophor RH 60), polyoxyl 35 castor oil (Cremophor EL), polyoxyl 5 castor oil, polyoxyl 9 castor oil, polyoxyl 15 castor oil, and d-α-tocopheryl polyethylene glycol 1000 succinate (TPGS), Solutol HS-15, PEG 300 caprylic/capric glycerides (Softigen 767), and PEG 400 caprylic/capric glycerides (Labrasol). Preferably, polyoxyl 35 in castor oil may be contained in said formulation in a concentration of from about 20% to about 75%. Most preferably, polyoxyl 35 castor oil is contained in said formulation in a concentration of about 50%. Representative examples of useful nonionic surfactants/emulsifiers include polysorbates such as polyoxyethylene sorbitan monooleate (polysorbate 80, Tween 80), polysorbate 65, polysorbate 65, polysorbate 61, polysorbate 60, polysorbate 40, polysorbate 21, polysorbate 20, polysorbate 81, polysorbate 85, and polysorbate 120, and polyoxyethylene stearates such as polyoxyl 8 stearate (PEG 400 monostearate), polyoxyl 2 stearate, polyoxyl 4 stearate, polyoxyl 6 stearate, polyoxyl 12 stearate, polyoxyl 20 stearate, polyoxyl 30 stearate, polyoxyl 40 stearate, polyoxyl 50 stearate, polyoxyl 100 stearate, polyoxyl 150 stearate, and polyoxyl 4 distearate, polyoxyl 8 distearate, polyoxyl 12 distearate, polyoxyl 32 distearate, polyoxyl 150 distearate. Preferably, herein the polyoxyethylene sorbitan monooleate is contained in said formulation in a concentration of from about 20% to about 50%. Most preferably, polyoxyethylene sorbitan monooleate is contained in said formulation in a concentration of 25%. Representative examples of useful co-surfactants include polyethylene glycol 400, polyethylene glycol 300, polyethylene glycol 200, polyethylene glycol 600, propylene glycol, and glycerin. Preferably, polyethylene glycol 400 is contained in said formulation in a concentration of from about 10% to about 45%. More preferably, polyethylene glycol 400 is contained in said formulation in a concentration of about 15%. Representative examples of useful co-stabilizers include benzyl alcohol, N,N-dimethylacetamide (DMA), dimethylsulfoxide (DMSO), 1-methyl-2-pyrrolodone (NMP), and ethanol. Preferably, benzyl alcohol is contained in said formulation in a concentration of from about 1% to about 15%. Most preferably, benzyl alcohol is contained in said formulation in a concentration of about 10%. Preferably, N,N-dimethylacetamide is contained in said formulation in a concentration of from about 1% to about 15%. More preferably, N,N-dimethylacetamide is contained in said formulation in a concentration of 5%. The pharmaceutical formulation of the present invention, after dilution with water, the formulation remains clear without precipitation and stable for 24 hours.

Generally, the pharmaceutical formulation is suitable for intravenous administration. Preferably, intravenous administration of the formulation of the present invention results in maximum plasma concentration of itraconazole of at least about 3 times higher than that from previously marketed brand Sporanox®.

The present invention is also directed to a pharmaceutical formulation of itraconazole, the formulation comprising itraconazole, a solubilizer in a concentration of from about 20% to about 75%, a nonionic surfactant/emulsifier in a concentration of from about 20% to about 50%, a co-surfactant in a concentration of from about 10% to about 45% and a stabilizer in a concentration of from about 1% to about 15%. In one aspect, the solubilizer is polyoxyl 35 castor oil which is contained in said formulation in a concentration of 50%. In one aspect, the nonionic surfactant/emulsifier is polyoxyethylene sorbitan monooleate and is contained in said formulation in a concentration of 25%. In one aspect, the co-surfactant is polyethylene glycol 400 and is contained in said formulation in a concentration of 15%. In one aspect, the stabilizer is selected from the group consisting of benzyl alcohol and is contained in said formulation in a concentration of about 10% and N,N-dimethylacetamide and is contained in said formulation in a concentration of about 5%.

The present invention is further directed to a pharmaceutical formulation of itraconazole, the formulation comprising itraconazole, polyoxyl 35 castor oil in a concentration of from about 20% to about 75%, polyoxyethylene sorbitan monooleate in a concentration of from about 20% to about 50%, polyethylene glycol 400 in a concentration of from about 10% to about 45% and benzyl alcohol in a concentration of from about 1% to about 15%. Preferably, the polyoxyl 35 castor oil is contained in said formulation in a concentration of about 50%. Preferably, the polyoxyethylene sorbitan monooleate is contained in said formulation in a concentration of about 25%. Preferably, the polyethylene glycol 400 is contained in said formulation in a concentration of about 15%. Preferably, the benzyl alcohol is contained in said formulation in a concentration of about 10%.

In one embodiment of the present invention, there is provided a co-solvent formulation of itraconazole suitable for intravenous administration. In a preferred aspect, the formulation contains 10 mg/g of itraconazole dissolved in 10% Benzyl alcohol, 50% Cremophor EL, 15% PEG 400, and 25% Polysorbate 80. After a 1:10 dilution with normal saline or D5W, a clear drug solution was obtained and remained clear for 24 hour at room temperature, which is necessary for intravenous infusion. A diluted drug formulation was successfully administered to rats without any signs of acute toxicity. A pharmacokinetic study also showed a superior bioavailability of this formulation when compared with the marketed Sporanox® Intravenous formulation. The co-solvent formulations of itraconazole of the present invention do not contain _-cyclodextrin but are capable of dissolving itraconazole in aqueous solutions for intravenous administration, as well as a much higher plasma drug concentrations after intravenous administration than the marketed Sporanox® Intravenous formulation.

The following examples are given for the purpose of illustrating various embodiments of the invention and are not meant to limit the present invention in any fashion.

EXAMPLE 1

Materials

Itraconazole was purchased from Sigma (St. Louis, Mo., USA). Sporanox® IV was purchased from Jassen Pharmaceuticals Inc. Tween 80, Cremophor EL, DMA, glycerin, PEG 400, and ethanol were also purchased from Sigma. DMSO was from EMD Chemicals (Gibbstown, N.J.), and Hydrochloride acid was purchased from Fisher Scientific (Fair Lawn, N.J., USA). All reagents were used as received. Double de-ionized water was generated by a Milli-Q® academic ultra-pure water purification system (Millipore, Bedford, Mass., USA).

EXAMPLE 2

Preparation of Itraconazole Formulation

Co-solvent formulations of itraconazole were prepared by dissolving itraconazole powder in a small quantity of either benzyl alcohol or DMA. A water bath heat (80-90° C.) may be applied to ensure complete drug dissolution. Surfactants such as Cremophor EL and Tween 80 were added followed by co-surfactant such as PEG 400 or properly glycol. Various solvent compositions were tested to determine the best suitable candidates. Each formulation was immediately tested for precipitation potential by 1:10 dilution of the formulation with either purified water or diluted hydrochloride acid (0.1N). Optimal formulations with no precipitation upon dilution with aqueous medium were further analyzed on itraconazole stability in the formulation.

EXAMPLE 3

Analysis of Itraconazole Using LC-MS/MS

Itraconazole concentrations in dosage formulations and in rat plasma were analyzed using a LC-MS/MS method. Chromatographic analysis was performed using an Agilent 1200 series HPLC system (Foster City, Calif.). Itraconazole and the internal standard (warfarin) were separated on a reverse phase XTerra MS-$C_{18}$ (50 mm×2.1 mm, 3.5 μm) in conjunction with an XTerra® MS $C_{18}$ guard column (20×3.9 mm, 3.5 μm). The mobile phases consisted of 2 mM ammonium acetate aqueous solution containing 0.1% formic acid (mobile phase A) and methanol with 0.1% formic acid (mobile phase B). A gradient elution starting with 40% mobile phase B was increased linearly to 100% mobile phase B over 5 minutes, kept constant at 100% B for 2 minutes, and then decreased to 40% B in 0.1 minutes and maintained the composition until the end of a run at 8.0 minutes. The flow rate was set at 0.3 mL/min. The column effluent was monitored using 3200 QTRAP® LC/MS/MS, which is a hybrid triple quadrupole linear ion trap equipped with a TurboIonSpray ion source. Pure nitrogen was generated by a Parker Balston Source 5000 Tri Gas Generator. The IonSpray heater was maintained at 650° C. with both the nebulizer gas and heater gas set to 80. IonSpray needle voltage was set to 4500 V, curtain gas was set to 10 psi, and collision CAD gas was set to medium.

Optimal multiple reaction monitoring (MRM) was used to detect transition ions from a specific precursor ion to product ion for itraconazole ([M+H]$^+$ m/z 707.3/392.4) and the internal standard ([M+H]$^+$ m/z 310.2/252.1), respectively. The collision energy was set at 25 and 49 eV for itraconazole and the internal standard, respectively. Other compound parameters were determined for each drug using the QTRAP instrument and version 1.5 of the Analyst® Software. Under these conditions, the retention time for itraconazole and the internal standard were 5.8 and 4.8 min, respectively (FIG. 1).

Stock solutions of itraconazole and the internal standard were dissolved in a 10-mL volumetric flask in methanol at 1.0 mg/mL, respectively. A series of standard working solutions containing itraconazole were prepared in blank rat plasma containing itraconazole concentrations of 10, 25, 50, 100, 250, 500, and 1000 ng/mL. Aliquots of plasma samples (100 μL) were extracted with 200 μL of ethyl acetate containing 500 ng/mL of the internal standard. The supernatant was injected onto the LC-MS/MS. The assay was linear for itraconazole concentration in the range of 10 ng/mL-1,000 ng/mL.

EXAMPLE 4

Animal Studies

Male Sprague-Dawley rats (250-320 g, Harlan Sprague Dawley, Inc., Indianapolis, Ind.) were housed in stainless steel cages and had free access to food and water. The rats were acclimated to the animal care facility for at least 7 days before the start of the study. To facilitate the withdrawal of timed, multiple blood samples from each animal, the right jugular vein of each animal was cannulated one day prior to drug administration. The cannulas were flushed daily with 0.5 mL sterile heparinized saline (100 units/ml). Under ketamine:acetopromazine:xylazine (50:3.3:3.3 mg/kg ip) anesthesia, silicone elastomer tubing (0.02×0.037 in) was inserted into the jugular vein, secured with a silk suture, and exteriorized in the dorsal infrascapular area. The surgical incision were prophylactically treated with nitrofurazone wound powder and closed with surgical staples.

Animals were allowed free access to food and water at all times. All in vivo studies were initiated between 8:00 am and 9:00 am to eliminate possible circadian variation. The control group (n=4) was given an intravenous 10 mg/kg administration of Sporanox® I.V. solution. A dosing drug solution was prepared by diluting one part of Sporanox® I.V. solution (10 mg/mL) with 2 parts of D5W. The solution was infused at 0.3 mL/min (i.e., 1 mg/min) using a Harvard infusion pump. The testing group (n=4) was given an intravenous 10 mg/kg administration of itraconazole formulated solution. The dosing drug solution was prepared by diluting one part of formulation A (10 mg/g) with 9 parts of D5W. The solution was infused at 1 mL/min (i.e., 1 mg/min). Immediately at the end of a dosing infusion, the time was counted. Multiple blood samples (0.25 mL) were collected (from the jugular vein cannula) at 12 predetermined times. An aliquot of each plasma sample was stored at −70° C. pending LC-MS/MS assay.

EXAMPLE 5

Pharmacokinetic and Statistical Data Analysis

Non-compartmental pharmacokinetic parameters were determined by classical techniques using the WinNonlin computer program. $C_{max}$—The maximum plasma concentration of drug was determined from the plasma drug concentration versus time profile. The terminal phase elimination half-life ($t_{1/2}$) was determined from the slope of the terminal linear segment of a semi-logarithmic plot of plasma drug concentration vs. time. AUC—The total area under the plasma concentration-time curve was determined by the trapezoidal rule using plasma drug concentration vs. time data from time zero to the last experimental time plus the excess area (from the last experimental time to time infinity). The excess area was calculated as 1.44×$t_{1/2}$× plasma concentration at the last experimental time. CL—The systemic clearance was determined as Dose/AUC. And Vss—The volume of distribution at steady-state was calculated as Dose/[AUMC/AUC$^2$], where AUMC is the area under the first moment plasma concentration time curve. Statistical differences between the mean values of Sporanox® IV and our formulation were determined by Student t-test. The statistical analysis was performed in SYSTAT computer program.

EXAMPLE 6

Development of Injectable Formulation of Itraconazole

Various compositions of surfactant and co-surfactant were evaluated for an optimal injectable formulation of itraconazole. Table 1 summarized such compositions. Almost all of these formulations were clear solutions at itraconazole concentration of 10 mg/mL, comparable with the marketed Sporanox® I.V. Injection. Some of the formulations precipitated after one month of storage at room temperature.

TABLE 1

Compositions of Selected Injectable Itraconazole Formulations

| Formula | Drug (mg) | DMA (µL) | Benzyl Alcohol (µL) | Cremophor EL (mg) | Tween 80 (mg) | PEG 400 (mg) | Appearance | 1:10 Dilution with D5W |
|---|---|---|---|---|---|---|---|---|
| #36 | 10 | 50 | | 950 | | | Clear | Clear |
| #37 | 10 | 50 | | 750 | | 200 | Clear | Clear |
| #40 | 10 | 50 | | 650 | | 300 | Clear | PPT |
| #50 | 10 | 50 | | 450 | 300 | 200 | Clear | Slight PPT |
| #51 | 10 | 50 | | 450 | 400 | | Clear | PPT |
| #52 | 10 | 100 | | 450 | | 450 | Cloudy | PPT |
| #56 | 10 | | 50 | 450 | 300 | 200 | Clear | Clear |
| #57 | 10 | | 100 | 500 | 250 | 150 | Clear | Clear |

It has been reported that itraconazole has high solubility in surfactant such as Tween 20 (solubility=1.19 mg/mL) and PEG 400 (solubility=2.14 mg/mL) (Rhee et al, 2007a; Hong et al, 2006). Unfortunately, there is difficulty with developing an injectable formulation of itraconazole because of the potential of drug precipitation upon dilution of a formulation with aqueous medium.

The present invention describes several optimal injectable formulations of itraconazole, where no precipitation was observed upon dilution with aqueous medium. For example, it was determined that maintaining a high Cremophor EL concentration in the formulation was crucial to keep itraconazole from precipitation during a long-term storage at room temperature, as well as upon 1:10 dilution with aqueous medium. For example, no precipitation was observed upon 1:10 dilution of a formulation containing 75% of Cremophor EL (Formulation #37) with water or acid.

Due to potential toxicity of Cremophor EL, its concentration was decreased and replaced with Tween 80. It was also determined that a certain percentage of PEG 400 in the formulation helps prevent aqueous precipitation. Therefore, an optimal formulation containing 10 mg/mL of itraconazole was formulated with 5% DMA, 45% Cremophor, 30% Tween 80 and 20% PEG 400. The formulation was successfully diluted with D5W at 1:10 dilution without any drug precipitation for at least 24 hours at room temperature. However, there was a very slight precipitation of itraconazole in the original dosage form after 2 weeks of storage at room temperature.

To resolve this issue, DMA was replaced with benzyl alcohol and formulated a similar 10 mg/g itraconazole injectable Formulation #57 containing 10% benzyl alcohol, 50% Cremophor, 25% Tween 80 and 15% PEG 400. No drug precipitation was observed upon storage at room temperature for at least 1 month, and upon 1:10 dilution with D5W, the solution was clear. The diluted solution was then used for further animal study comparing pharmacokinetic equivalency between the formulation and the brand product.

EXAMPLE 7

Pharmacokinetic Analysis

Figure 2:
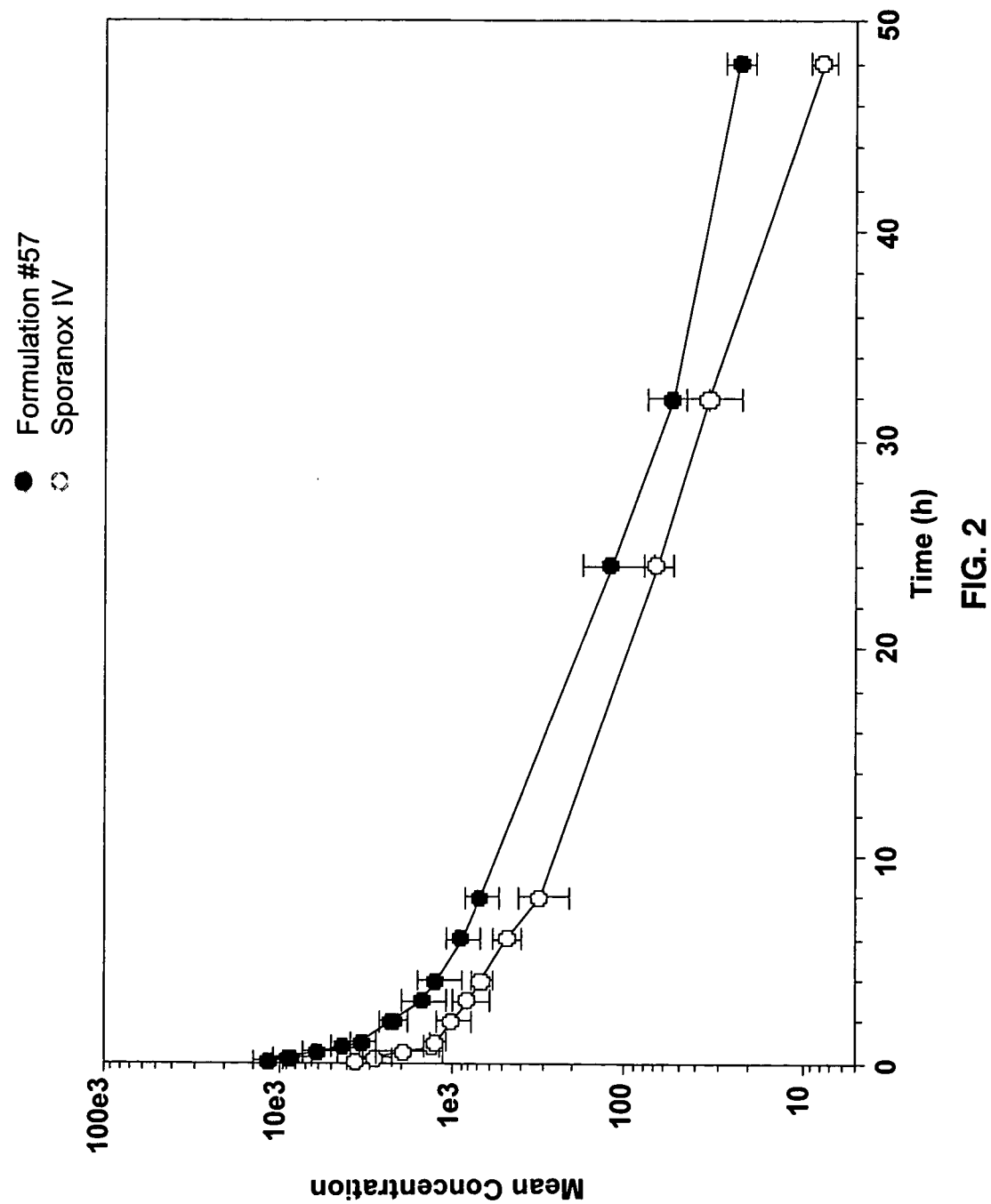
FIG. 2 shows a mean (±SD, n=4) comparative plasma itraconazole concentration versus time profiles after intravenous administration of a 10 mg/kg dose of either the Formulation #57 of the present invention or Sporanox® I.V. to male Sprague-Dawley rats.

An in vivo pharmacokinetic study was performed to evaluate whether the developed injectable formulation (#57) of itraconazole had similar a pharmacokinetic profile to that of the product, Sporanox® I.V. FIG. 2 shows a mean plasma concentration versus time curve of itraconazole following 10 mg/kg intravenous injection of either Formulation #57 or Sporanox® I.V. Itraconazole concentrations in plasma were significantly higher with Formulation #57 than that of Sporanox® I.V.

Pharmacokinetic parameters of itraconazole are shown in Table 2. The injectable itraconazole formulation (#57) of the present invention had a significantly higher AUC (2.2-fold higher) and $C_{max}$ (3.2-fold higher) as compared with Sporanox® I.V. The data suggests that this injectable itraconazole formulation was more systemically bioavailable, which are clearly shown to be advantageous in clinical applications of the drug formulation. The difference in the bioavailability between the itraconazole formulation of the present invention and Sporanox® I.V. may be attributed to the complexation of itraconazole with HP-3-CD of the Sporanox® I.V. formulation. The complexation may have significantly increased itraconazole clearance as well as its volume of distribution. In fact, this pharmacokinetic data obtained from the Sporanox® I.V. formulation was in close consistency with published data from Shin et al (2004), who used the same rat model and dosing schedule of the Sporanox® I.V. formulation.

TABLE 2

Mean (SD) Pharmacokinetic Parameters of Itraconazole following Intravenous Administration of Formulation #57 versus Sporanox at 10 mg/kg Dose to Male Sprague-Dawley Rats

| Parameter$^a$ | Sporanox | Formulation #57 | P Value |
|---|---|---|---|
| N | 4 | 4 | |
| $T_{1/2}$ (hr) | 7.27 ± 1.0 | 7.35 ± 0.58 | 0.904 |
| AUC (ng h/mL) | 10,715 ± 1,486 | 24,485 ± 4,503 | 0.001 |

TABLE 2-continued

Mean (SD) Pharmacokinetic Parameters of Itraconazole following Intravenous Administration of Formulation #57 versus Sporanox at 10 mg/kg Dose to Male Sprague-Dawley Rats

| Parameter[a] | Sporanox | Formulation #57 | P Value |
| --- | --- | --- | --- |
| $C_{max}$ (ng/mL) | 4,171 ± 371 | 13,348 ± 2,383 | 0.000 |
| $V_{ss}$ (mL/kg) | 7,110 ± 1,405 | 2,672 ± 523 | 0.007 |
| CL (mL/hr/kg) | 946 ± 125 | 420 ± 82 | 0.000 |

[a]N = number of rats employed; $T_{1/2}$ = terminal biological half-life; AUC = total area under the plasma concentration vs time curve; $C_{max}$ = predicted maximum drug concentration in plasma; $V_{ss}$ = volume of distribution at steady-state; CL = total body clearance.
P values were obtained using a Two-sample t-test.

It is also worth noting that the terminal elimination half-life of itraconazole remain the same between the two formulations. This is true because itraconazole from the complex would eventually be released to plasma and exhibits the same characteristics as the formulation of the present invention. The pharmacokinetic data clearly indicates that the formulation of the present invention is superior to the Sporanox® I.V. formulation in terms of bioavailability. A significantly higher itraconazole plasma concentration resulted with the formulation of the present invention which would be of a great clinical application against fungal infection.

EXAMPLE 8

Acute Toxicity

All animals who received 10 mg/kg Sporanox® I.V. formulation or the Formulation #57 showed no signs of discomfort or any cardiovascular and respiratory disorders after the drug administration and throughout the study period. There was no change in body weight monitored for a 7-day period after drug administration.

EXAMPLE 9

Drug Stability

Itraconazole stability in the dosage formulation #57 was evaluated for long-term storage at room temperature. Itraconazole stability was tested after diluting the formulation with D5W. The formulation of the present invention was cleared after 1:10 dilution with D5W, and the drug solution was stable after 48 hours. There was no significant degradation of itraconazole for up to 6 months of storage at room temperature. Table 3 showed itraconazole concentration (measured by the LC-MS/MS method) in the dosage formulation #57 after long term storage. The data indicates that the present invention was free of itraconazole precipitation for up to 6 months. Itraconazole concentration decreased by 9 month due to the drug precipitation. With respect to general product shelf-life of 2 years requirement, long-term stability of the present invention may be significantly improved by reducing itraconazole concentration from the current 10 mg/g to 5 mg/g for commercial applications. Table 3 represents a single formulation, and each measuring point represent triplicate analytical measurements of the drug concentration

TABLE 3

Long-term Stability of Itraconazole Formulation #57 Under Room Temperature

| Tests | 3 Month Storage | 6 Month Storage | 9 Month Storage |
| --- | --- | --- | --- |
| Itraconazole concentration | 13.17 mg/mL | 13.34 mg/mL | 5.74 mg/mL |
| Physical appearance | Clear solution | Clear solution | Cloudy, drug precipitation |

CONCLUSION

The present invention describes the development of a co-solvent formulation of itraconazole suitable for intravenous administration. The formulation #57 contains 10 mg/g of itraconazole dissolved in 10% Benzyl alcohol, 50% Cremophor EL, 15% PEG 400, and 25% Polysorbate 80. Upon 1:10 dilution with D5W, the resulting solution remained clear without precipitation and stable for 24 hours. The diluted solution was successfully administered intravenously through infusion to rats without any signs of acute toxicity. The formulation of the present invention also demonstrated superior pharmacokinetic profiles than the Sporanox® I.V. formulation in terms of a higher maximum plasma concentrations of itraconazole and higher area under the plasma concentration time curve.

The following references were cited herein:
1. Saag M S, Dismukes W E. *Antimicrob. Agents Chemother.*, 32:1-8, 1988.
2. Odds et al., *Antimicrob. Agents Chemother.*, 44:3180-3183, 2000.
3. Beule K and Gestel J. Pharmacology of itraconazole. *Drugs*, 61:27-37, 2001.
4. Boogaerts et al., *Antimicrob. Agents Chemother.*, 45:981-985, 2001.
5. Groll et al., *Antimicrob. Agents Chemother.*, 46:2554-2563, 2002.
6. Picardi et al., *Haematologica*, 88, ELT01, 2003.
7. Heykants et al., *Mycoses*, 32(Suppl. 1):67-87, 1989.
8. Jung et al., *Int. J. Pharm.*, 187:209-218, 1999.
9. Peeters et al., *J. Pharm. Sci.*, 91:1414-1422, 2002.
10. Rhee et al., *Arch. Pharm. Res.*, 30: 114-123, 2007.
11. Rhee et al., *Arch. Pharm. Res.*, 30: 240-248, 2007.
12. Hong et al., *J. Control. Release*, 110:332-338, 2006.
13. Kim et al., *Int. J. Pharm.*, 383:209-215, 2010.
14. Rabinow et al., *Int. J. Pharm.*, 339:251-260, 2007.
15. Yi et al., *J. Control. Release*, 117:59-67, 2007.

Any patents or publications mentioned in this specification are indicative of the levels of those skilled in the art to which the invention pertains. Further, these patents and publications are incorporated by reference herein to the same extent as if each individual publication was specifically and individually incorporated by reference. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:
1. A pharmaceutical formulation of itraconazole, said formulation suitable for intravenous administration and consisting of:
    itraconazole;

polyoxyl 35 castor oil;
a non-ionic surfactant/emulsifier;
a co-surfactant; and,
a stabilizer, wherein said non-ionic surfactant/emulsifier is selected from the group consisting of polyoxyethylene sorbitan monooleate, Polysorbate 20, and Polyoxyl 8 stearate.

2. The pharmaceutical formulation of claim 1, wherein said itraconazole is contained in said formulation in a concentration range from about 2 mg/mL to about 20 mg/ml.

3. The pharmaceutical formulation of claim 1, wherein said polyoxyl 35 castor oil is contained in said formulation in a concentration from about 20% to about 75%.

4. The pharmaceutical formulation of claim 3, wherein said polyoxyl 35 castor oil is contained in said formulation in a concentration of about 50%.

5. The pharmaceutical formulation of claim 1, wherein said polyoxyethylene sorbitan monooleate is contained in said formulation in a concentration from about 20% to about 50%.

6. The pharmaceutical formulation of claim 5, wherein said polyoxyethylene sorbitan monooleate is contained in said formulation in a concentration of about 25%.

7. The pharmaceutical formulation of claim 1, wherein said co-surfactant is selected from the group consisting of polyethylene glycol 400, polyethylene glycol 300, Propylene glycol and Glycerin.

8. The pharmaceutical formulation of claim 7, wherein said polyethylene glycol 400 is contained in said formulation in a concentration from about 10% to about 45%.

9. The pharmaceutical formulation of claim 8, wherein said polyethylene glycol 400 is contained in said formulation in a concentration of about 15%.

10. The pharmaceutical formulation of claim 1, wherein said stabilizer is selected from the group consisting of benzyl alcohol and N, N-dimethylacetamide, dimethylsulfoxide (DMSO), 1-methyl-2-pyrrolodone (NMP), and ethanol.

11. The pharmaceutical formulation of claim 10, wherein said benzyl alcohol is contained in said formulation in a concentration from about 1% to about 15%.

12. The pharmaceutical formulation of claim 11, wherein said benzyl alcohol is contained in said formulation in a concentration of about 10%.

13. The pharmaceutical formulation of claim 10, wherein said N, N-dimethylacetamide is contained in said formulation in a concentration from about 1% to about 15%.

14. The pharmaceutical formulation of claim 13, wherein said N, N-dimethylacetamide is contained in said formulation in a concentration of about 5%.

15. The pharmaceutical formulation of claim 1, wherein after dilution with water, the formulation remains clear without precipitation and stable for 24 hours.

16. The pharmaceutical formulation of claim 1, wherein intravenous administration of said formulation results in maximum plasma concentration of itraconazole of at least about 3 times higher than that from a commercially available itraconazole formulation comprising hydroxylpropyl-β cyclodextrin.

17. A pharmaceutical formulation of itraconazole, said formulation suitable for intravenous administration and consisting of itraconazole in a concentration range from about 2 mg/mL to about 20 mg/mL, polyoxyl 35 castor oil in a concentration from about 20% to about 75%, a non-ionic surfactant/emulsifier in a concentration from about 20% to about 50%, a co-surfactant in a concentration from about 10% to about 45% and a stabilizer in a concentration from about 1% to about 15%, wherein said non-ionic surfactant/emulsifier is selected from the group consisting of polyoxyethylene sorbitan monooleate, Polysorbate 20, and Polyoxyl 8 stearate.

18. The pharmaceutical formulation of claim 17, wherein said polyoxyl 35 castor oil is contained in said formulation in a concentration of about 50%.

19. The pharmaceutical formulation of claim 17, wherein said non-ionic surfactant/emulsifier is polyoxyethylene sorbitan monooleate.

20. The pharmaceutical formulation of claim 19, wherein said polyoxyethylene sorbitan monooleate is contained in said formulation in a concentration of about 25%.

21. The pharmaceutical formulation of claim 17, wherein said co-surfactant is polyethylene glycol 400.

22. The pharmaceutical formulation of claim 21, wherein said polyethylene glycol 400 is contained in said formulation in a concentration of about 15%.

23. The pharmaceutical formulation of claim 17, wherein said stabilizer is selected from the group consisting of benzyl alcohol, dimethylsulfoxide (DMSO), 1-methyl-2-pyrrolodone (NMP), ethanol and N, N-dimethylacetamide.

24. The pharmaceutical formulation of claim 23, wherein said benzyl alcohol is contained in said formulation in a concentration of about 10%.

25. The pharmaceutical formulation of claim 23, wherein said N, N-dimethylacetamide is contained in said formulation in a concentration of about 5%.

26. A pharmaceutical formulation of itraconazole, said formulation suitable for intravenous administration and consisting of itraconazole in a concentration from about 0.2% to about 2%, polyoxyl 35 castor oil in a concentration from about 20% to about 75%, polyoxyethylene sorbitan monooleate in a concentration from about 20% to about 50%, polyethylene glycol 400 in a concentration from about 10% to about 45% and benzyl alcohol in a concentration from about 1% to about 15%.

27. The pharmaceutical formulation of claim 26, wherein said polyoxyl 35 castor oil is contained in said formulation in a concentration of 50%.

28. The pharmaceutical formulation of claim 26, wherein said polyoxyethylene sorbitan monooleate is contained in said formulation in a concentration of about 25%.

29. The pharmaceutical formulation of claim 26, wherein said polyethylene glycol 400 is contained in said formulation in a concentration of about 15%.

30. The pharmaceutical formulation of claim 26, wherein said benzyl alcohol is contained in said formulation in a concentration of about 10%.

* * * * *